US011945764B2

(12) United States Patent
Jansone-Popova et al.

(10) Patent No.: US 11,945,764 B2
(45) Date of Patent: Apr. 2, 2024

(54) EFFICIENT SYNTHESIS OF DIGLYCOLAMIDE MOLECULES

(71) Applicant: UT-Battelle, LLC, Oak Ridge, TN (US)

(72) Inventors: Santa Jansone-Popova, Knoxville, TN (US); Ilja Popovs, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 17/835,028

(22) Filed: Jun. 8, 2022

(65) Prior Publication Data

US 2023/0002311 A1  Jan. 5, 2023

Related U.S. Application Data

(60) Provisional application No. 63/208,591, filed on Jun. 9, 2021.

(51) Int. Cl.
| | | |
|---|---|---|
| *C07C 231/02* | (2006.01) | |
| *C07D 207/12* | (2006.01) | |
| *C07D 211/40* | (2006.01) | |

(52) U.S. Cl.
CPC .......... *C07C 231/02* (2013.01); *C07D 207/12* (2013.01); *C07D 211/40* (2013.01)

(58) Field of Classification Search
CPC .... C07C 231/02; C07D 207/12; C07D 211/40
See application file for complete search history.

(56) References Cited

U.S. PATENT DOCUMENTS

| | | | |
|---|---|---|---|
| 4,379,928 A | 4/1983 | Theodoropulos | |
| 11,040,296 B2 | 6/2021 | Brigham et al. | |
| 2010/0010244 A1* | 1/2010 | Krull | C07C 231/02 554/61 |
| 2012/0088885 A1 | 4/2012 | Krull et al. | |
| 2013/0123534 A1 | 5/2013 | Sakaki et al. | |
| 2020/0290998 A1 | 9/2020 | Blanc et al. | |
| 2022/0002229 A1 | 1/2022 | Jansone-Popova et al. | |
| 2022/0002840 A1 | 1/2022 | Jansone-Popova et al. | |

OTHER PUBLICATIONS

Fein, M.L., et al., "N-Substituted Lactamides", Journal of the American Chemical Society, May 5, 1953, pp. 2097-2099, vol. 75.
Invitation to Pay Additional Fees dated Aug. 25, 2022 PCT/US 2022/032616, 3 pages.
Leoncini, A., et al., "Preparation of Diglycolamides via Schotten-Baumann Approach and Direct Amidation of Esters", Synlett 2016, Accepted after revision Jun. 11, 2016, Published online Jul. 13, 2016, pp. 2463-2466, 17.

International Search Report and Written Opinion dated Oct. 27, 2022 Application No. PCT/US2022/032616, 12 pages.

\* cited by examiner

*Primary Examiner* — Timothy R Rozof
(74) *Attorney, Agent, or Firm* — Scully, Scott, Murphy & Presser, P.C.

(57) ABSTRACT

A method for producing a diglycolamide molecule having the formula:

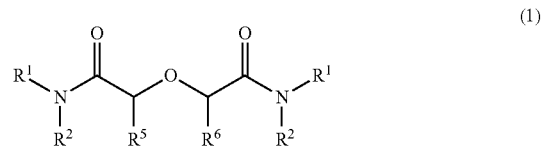

(1)

wherein $R^1$ and $R^2$ are independently selected from alkyl groups (R) and acyl groups (C(O)R) in which the alkyl groups (R) contain 1-30 carbon atoms and optionally contain an ether or thioether linkage between carbon atoms, and $R^5$ and $R^6$ are independently selected from hydrogen atom and alkyl groups containing 1-3 carbon atoms; and one or both pairs of $R^1$ and $R^2$ are optionally interconnected to form a ring; the method comprising: combining a diglycolic acid molecule (A) and a secondary amine (B) to form a salt intermediate (C), and heating the salt intermediate (C) to a temperature of 100° C. to 300° C. to form the diglycolamide of Formula (1) in a dehydration process, wherein the method is shown schematically as follows:

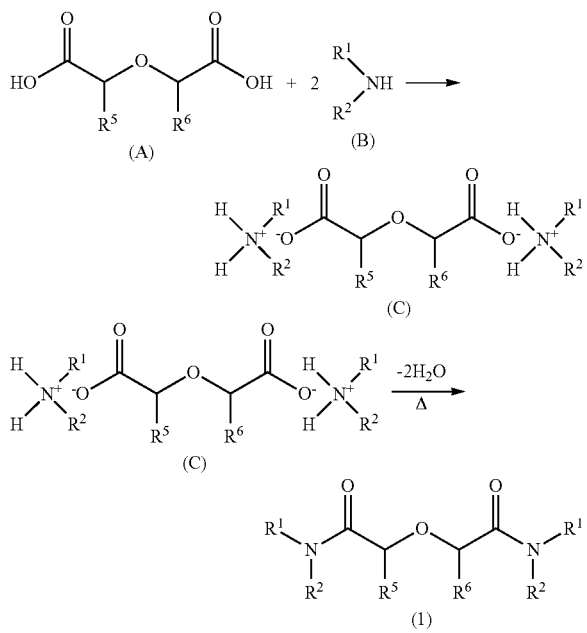

8 Claims, 4 Drawing Sheets

EFFICIENT SYNTHESIS OF DIGLYCOLAMIDE MOLECULES

CROSS REFERENCE TO RELATED APPLICATION

The present application claims benefit of U.S. Provisional Application No. 63/208,591, filed on Jun. 9, 2021, all of the contents of which are incorporated herein by reference.

STATEMENT REGARDING FEDERALLY SPONSORED RESEARCH

This invention was made with government support under Prime Contract No. DE-AC05-00OR22725 awarded by the U.S. Department of Energy. The government has certain rights in the invention.

FIELD OF THE INVENTION

The present invention generally relates to synthetic methods for the preparation of diglycolamide molecules, wherein the diglycolamide molecules may be symmetric or asymmetric.

BACKGROUND OF THE INVENTION

Diglycolamides (DGAs) are organic extractants used in the separation of f-elements, typically to separate lanthanides into groups or one from another, or to separate lanthanides from actinides. Despite the increased research activity and use of diglycolamides in recent years, their cost remains high. For example, one kilogram of N,N,N',N'-tetraoctyl diglycolamide (TODGA) may cost upwards of five or six thousand U.S. dollars. The high cost of DGAs is a direct result of the complex and costly processes currently in use for their synthesis. For example, the conventional process for producing symmetrical DGAs is as follows, as also shown schematically in FIG. 1: First, diglycolic acid is converted into diglycolyl chloride using, for example, thionyl chloride as a reagent. In this reaction, toxic and corrosive hydrochloric (HCl) gas is produced as a byproduct, which thus requires special equipment and a special set-up to ensure a safe working environment. As another example, the conventional process for producing asymmetrical DGAs is a four-step convergent synthesis shown schematically in FIG. 2. A key drawback of this synthetic method is the use of sodium hydride (NaH) as a base to promote nucleophilic substitution reaction between glycolamide and alkyl chloride. In this reaction, flammable hydrogen ($H_2$) gas is produced as a byproduct, which thus requires a special protocol to ensure a safe working environment.

With the demand for DGAs increasing, the cost of DGAs may decrease to some extent, but not enough to make industrial scale production of DGAs cost-effective. Alternative processes that could substantially lower the cost of producing DGAs has remained elusive. Thus, such a process would represent a significant advance in the art of DGA production.

SUMMARY OF THE INVENTION

In a first aspect, the present disclosure is directed to a lower-cost and more direct method for producing symmetric DGAs of the formula:

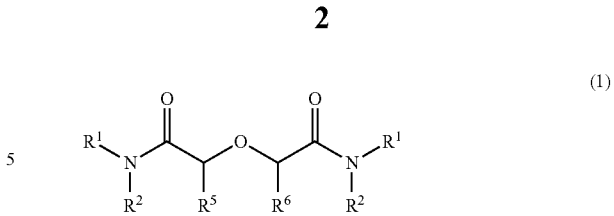

In Formula (1), $R^1$ and $R^2$ are independently selected from alkyl groups (R) and acyl groups (C(O)R) in which the alkyl groups (R) contain 1-30 carbon atoms and optionally contain an ether or thioether linkage between carbon atoms, and $R^5$ and $R^6$ are independently selected from hydrogen atom and alkyl groups containing 1-3 carbon atoms; and one or both pairs of $R^1$ and $R^2$ are optionally interconnected to form a ring.

The method for producing a DGA of Formula (1) is a one-pot synthesis that proceeds by combining a diglycolic acid molecule (A) and a secondary amine (B) to form a salt intermediate (C), and heating the salt intermediate (C) to a temperature of 100° C. to 300° C. to form the diglycolamide of Formula (1) in a dehydration process. The method is shown schematically as follows:

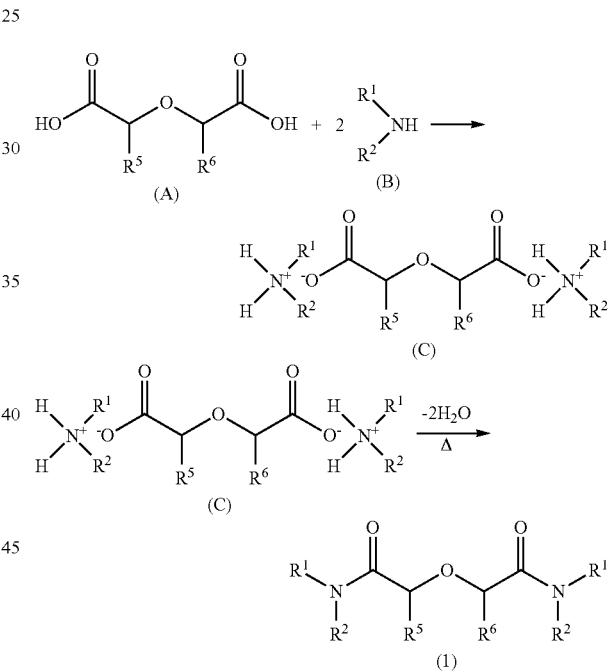

In a second aspect, the present disclosure is directed to a lower-cost and more direct method for producing symmetric and asymmetric DGAs of the formula:

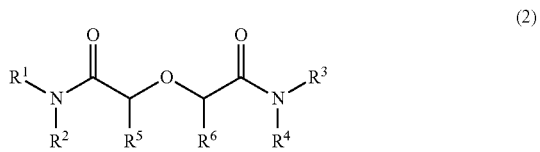

In Formula (2), $R^1$, $R^2$, $R^3$, and $R^4$ are independently selected from alkyl groups (R) and acyl groups (C(O)R) in which the alkyl groups (R) contain 1-30 carbon atoms and optionally contain an ether or thioether linkage between carbon atoms, and $R^5$ and $R^6$ are independently selected from hydrogen atom and alkyl groups containing 1-3 carbon atoms; $R^1$ and $R^2$ are optionally interconnected to form a ring; and $R^3$ and $R^4$ are optionally interconnected to form a ring.

The method for producing a DGA of Formula (2) is a three-step convergent synthesis that proceeds according to the following steps:

(i) combining a glycolic acid molecule (D) and a first secondary amine (B) to form a salt intermediate (E), and heating the salt intermediate to a temperature of 100° C. to 300° C. to result in production of a first reactant (F), according to the following scheme:

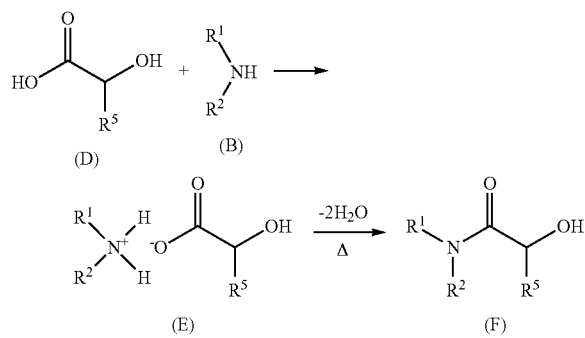

(ii) reacting a molecule (G) with a second secondary amine (B') to form a second reactant (H), according to the following scheme:

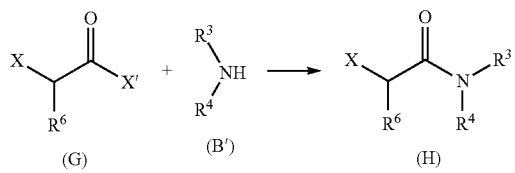

(iii) reacting the first reactant (F) and second reactant (H) in the presence of a base of sufficient strength to deprotonate first reactant (F) according to the following scheme to form the diglycolamide of Formula (2):

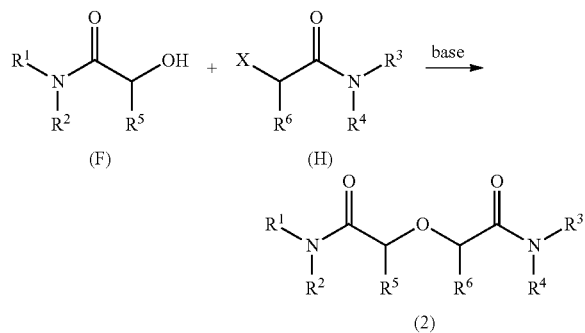

wherein X is a halogen atom or pseudo-halogen atom, and X' is a halogen atom.

In a third aspect, the present disclosure is directed to a lower-cost and more direct method for producing cyclic DGAs of the formula:

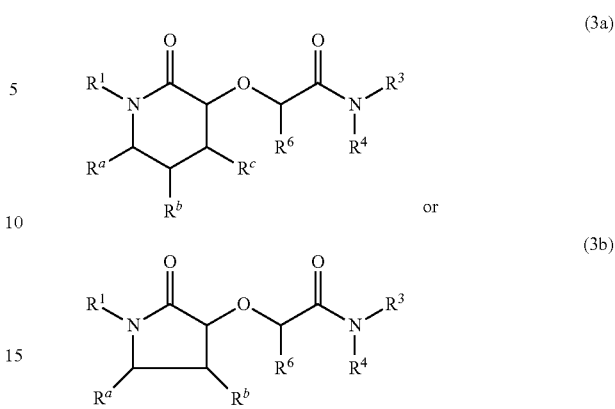

In Formulas (3a) and (3b), $R^1$, $R^3$, and $R^4$ are independently selected from alkyl groups (R) and acyl groups (C(O)R) in which the alkyl groups (R) contain 1-30 carbon atoms and optionally contain an ether or thioether linkage between carbon atoms; $R^6$ is selected from hydrogen atom and alkyl groups containing 1-3 carbon atoms; $R^a$, $R^b$, and $R^c$ are independently selected from hydrogen atom, alkyl groups (R), acyl groups (C(O)R), amide groups (C(O)NR$_2$), alkoxide groups (OR), and amine groups (NR$_2$) in which the alkyl groups (R) independently contain 1-30 carbon atoms and optionally contain an ether or thioether linkage between carbon atoms; $R^4$ and $R^6$ are optionally interconnected to form a ring; and $R^3$ and $R^4$ are optionally interconnected to form a ring.

The method for producing a DGA of Formula (3) proceeds by reacting reactant (J) and reactant (H) with a base of sufficient strength to deprotonate reactant (J) to form the cyclic diglycolamide of Formula (3a) or (3b), according to either of the following synthetic scheme, respectively:

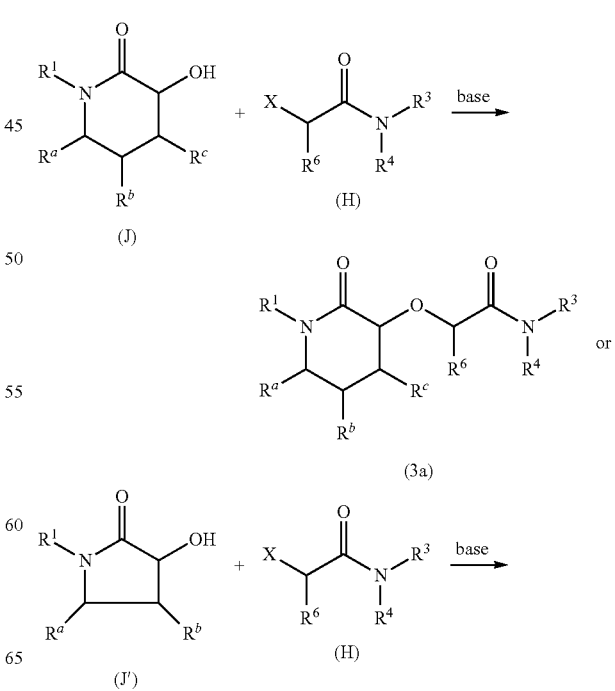

-continued

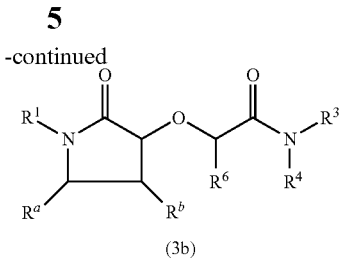

(3b)

In the above schemes, X is a halogen atom or pseudo-halogen atom.

DETAILED DESCRIPTION OF THE INVENTION

Figure 1:
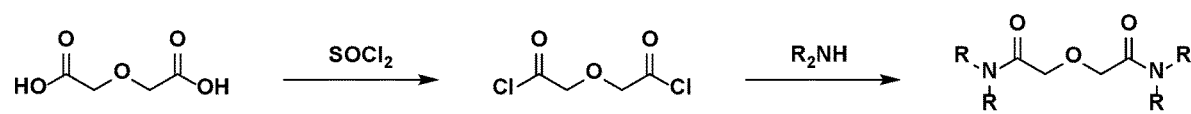
FIG. 1 is a schematic showing a conventional process for producing symmetrical diglycolamide (DGA) compounds.
Figure 2:
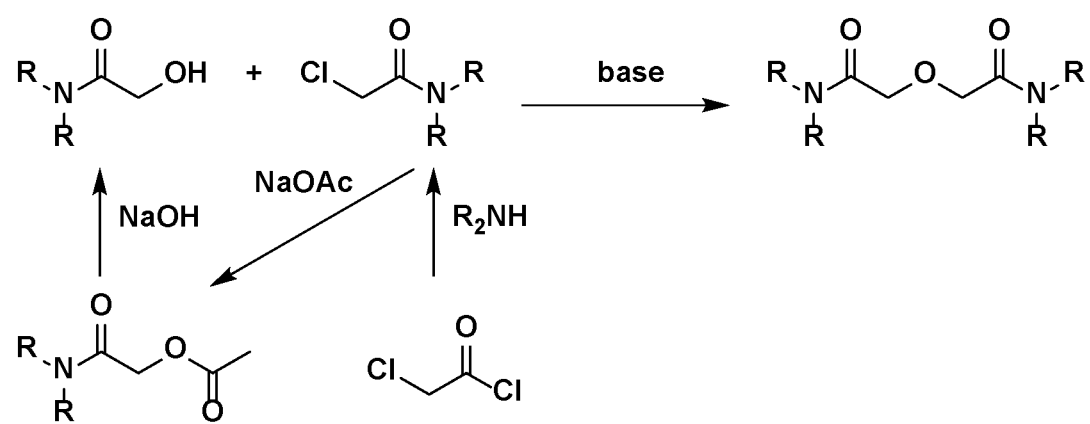
FIG. 2 is a schematic showing a conventional process for producing asymmetrical and symmetrical DGA compounds.

The term "alkyl group", as used herein and denoted by the group R, is a saturated hydrocarbon group that may be linear, branched, or cyclic. The alkyl group typically contains 1-30 carbon atoms. In different embodiments, one or more of the alkyl groups may contain, for example, 1, 2, 3, 4, 5, 6, 7, 8, 9, 10, 12, 15, 18, 20, 22, 24, 26, 28, or 30 carbon atoms, or a number of carbon atoms within a particular range bounded by any two of the foregoing carbon numbers (e.g., 1-30, 2-30, 3-30, 4-30, 6-30, 8-30, 10-30, 12-30, 1-20, 6-20, 8-20, 10-20, or 12-20 carbon atoms). Alkyl groups in different compounds described herein, or in different positions of a compound, may possess the same or different number (or preferred range thereof) of carbon atoms in order to independently adjust or optimize such properties as the complexing ability, extracting (extraction affinity) ability, selectivity ability, or third phase prevention ability of the compound.

In one set of embodiments, the alkyl group is composed solely of carbon and hydrogen (i.e., without containing any heteroatoms, such as fluorine, oxygen, sulfur, or nitrogen). Some examples of linear alkyl groups include methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-eicosyl, n-docosyl, n-tetracosyl, n-hexacosyl, n-octacosyl, and n-triacontyl groups. Some examples of branched alkyl groups include isopropyl (2-propyl), isobutyl (2-methylprop-1-yl), sec-butyl (2-butyl), t-butyl (1,1-dimethylethyl-1-yl), 2-pentyl, 3-pentyl, 2-methylbut-1-yl, isopentyl (3-methylbut-1-yl), 1,2-dimethylprop-1-yl, 1,1-dimethylprop-1-yl, neopentyl (2,2-dimethylprop-1-yl), 2-hexyl, 3-hexyl, 2-methylpent-1-yl, 3-methylpent-1-yl, isohexyl (4-methylpent-1-yl), 1,1-dimethylbut-1-yl, 1,2-dimethylbut-1-yl, 2,2-dimethylbut-1-yl, 2,3-dimethylbut-1-yl, 3,3-dimethylbut-1-yl, 1,1,2-trimethylprop-1-yl, 1,2,2-trimethylprop-1-yl, isoheptyl, isooctyl, and the numerous other branched alkyl groups having up to 20 or 30 carbon atoms, wherein the "1-yl" suffix represents the point of attachment of the group. Some examples of cyclic alkyl (cycloalkyl) groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane).

In another set of embodiments, the alkyl group may (i.e., optionally) be substituted with one or more fluorine atoms to result in partial or complete fluorination of the alkyl group. As an example, an n-octyl group may be substituted with a single fluorine atom to result in, for example, a 7-fluorooctyl or 8-fluorooctyl group, or substituted with two or more fluorine atoms to result in, for example, 7,8-difluorooctyl, 8,8-difluorooctyl, 8,8,8-trifluorooctyl, or perfluorooctyl group.

In another set of embodiments, the alkyl group may contain a single ether (—O—) or thioether (—S—) linkage connecting between carbon atoms in the alkyl group. An example of a hydrocarbon group containing a single ether or thioether group is —$(CH_2)_2$—X—$(CH_2)_7CH_3$, wherein X represents O or S.

In a first aspect, the present disclosure is directed to a lower-cost and more direct method for producing symmetric DGAs of the formula:

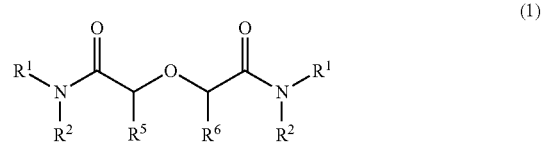

(1)

The variables $R^1$ and $R^2$ in Formula (1) are independently selected from alkyl groups (R) and acyl groups (C(O)R) in which the alkyl groups (R) contain 1-30 carbon atoms and optionally contain an ether or thioether linkage between carbon atoms, as described above. In some embodiments, $R^1$ and $R^2$ are structurally different. In other embodiments, $R^1$ and $R^2$ are structurally equivalent.

In one set of embodiments, $R^1$ and $R^2$ in Formula (1) are independently selected from linear, branched, and/or cyclic alkyl groups (R) containing 1-30 carbon atoms or a number of carbon atoms within a range therein, e.g., 2-30, 3-30, 4-30, 6-30, 8-30, 10-30, 12-30, 1-20, 6-20, 8-20, 10-20, 12-20, 1-12, 6-12, 8-12, 1-6, 2-6, or 3-6 carbon atoms. In one set of embodiments, $R^1$ and/or $R^2$ are alkyl groups composed of only carbon and hydrogen atoms, i.e., without containing any heteroatoms, such as fluorine, oxygen, sulfur, or nitrogen. In another set of embodiments, $R^1$ and/or $R^2$ are alkyl groups containing partial or complete fluorination. In another set of embodiments, one or both of $R^1$ and $R^2$ contain an ether or thioether linkage between carbon atoms, which may be in the absence or presence of fluorination of the alkyl group. In some embodiments, $R^1$ is equivalent to (same as) $R^2$ in carbon number, structure, or both. In other embodiments, $R^1$ is different from $R^2$ in carbon number, structure, or both. For example, $R^1$ may be an alkyl group containing 1-3 carbon atoms and $R^2$ may be an alkyl group containing 4-30 carbon atoms.

In another set of embodiments, one or both of $R^1$ and $R^2$ in Formula (1) are independently selected from C(O)R groups in which R is a linear, branched, and/or cyclic alkyl group (R) containing 1-30 carbon atoms or a number of carbon atoms within a range therein, e.g., 2-30, 3-30, 4-30, 6-30, 8-30, 10-30, 12-30, 1-20, 6-20, 8-20, 10-20, 12-20, 1-12, 6-12, 8-12, 1-6, 2-6, or 3-6 carbon atoms. In one set of embodiments, $R^1$ and/or $R^2$ are C(O)R groups in which R is selected from alkyl groups composed of only carbon and hydrogen atoms, i.e., without containing any heteroatoms, such as fluorine, oxygen, sulfur, or nitrogen. In another set of embodiments, $R^1$ and/or $R^2$ are C(O)R groups in which R is selected from alkyl groups containing partial or complete fluorination. In another set of embodiments, one or both of $R^1$ and $R^2$ are C(O)R groups in which R contains an ether or thioether linkage between carbon atoms, which may be in the absence or presence of fluorination of the alkyl group (R). In some embodiments, the alkyl group (R) in C(O)R in $R^1$ is equivalent to (same as) the alkyl group (R) in C(O)R in $R^2$ in carbon number, structure, or both. In other embodiments, the alkyl group (R) in C(O)R in $R^1$ is different from the alkyl group (R) in C(O)R in $R^2$ in carbon number, structure, or both. For example, $R^1$ may be a CO(R) group in which R is an alkyl group containing 1-3 carbon atoms and $R^2$ may be a C(O)R group in which R is an alkyl group containing 4-30 carbon atoms.

In another set of embodiments, a portion of $R^1$ and/or $R^2$ groups in Formula (1) are independently selected from linear, branched, and/or cyclic alkyl groups (R) containing 1-30 carbon atoms, and a portion of $R^1$ and/or $R^2$ groups are independently selected from C(O)R groups, thereby resulting in a compound of Formula (1) containing a mixture of R and C(O)R groups. For example, $R^1$ may be selected as an R group and $R^2$ may be selected as a C(O)R group.

Moreover, one or both pairs of $R^1$ and $R^2$ in Formula (1) are optionally interconnected to form a ring. The ring is typically a five- or six-membered ring. For example, $R^1$ and $R^2$ can each be selected as ethyl groups followed by interconnection at the terminal carbon atom of each ethyl group, thus resulting in formation of a five-membered ring (specifically, a pyrrolidinyl ring). Alternatively, one or both of $R^1$ and $R^2$ can be selected as a C(O)R group, thereby resulting in a lactam or succinimide ring. In the case of two rings being present, the rings may be the same or different in size and/or structure.

The variables $R^5$ and $R^6$ in Formula (1) are independently selected from hydrogen atom and alkyl groups (R') containing 1-3 carbon atoms. In some embodiments, precisely or at least one of $R^5$ and $R^6$ is a hydrogen atom, or $R^5$ and $R^6$ may both be hydrogen atoms. In other embodiments, precisely or at least one of $R^5$ and $R^6$ is an alkyl group (R') containing 1-3 carbon atoms, or $R^5$ and $R^6$ may both be R'. In the case where $R^5$ and $R^6$ are both alkyl groups (R') containing 1-3 carbon atoms, $R^5$ and $R^6$ may be the same or different. In some embodiments, precisely or at least one of $R^5$ and $R^6$ is a methyl group, or $R^5$ and $R^6$ may both be methyl groups. In some embodiments, one of $R^5$ and $R^6$ is an alkyl group and one of $R^5$ and $R^6$ is a hydrogen atom. Notably, any of the above selections and combinations provided for $R^5$ and $R^6$ groups can be combined with any of the selections and combinations provided earlier above for $R^1$ and $R^2$ groups.

Figure 3:
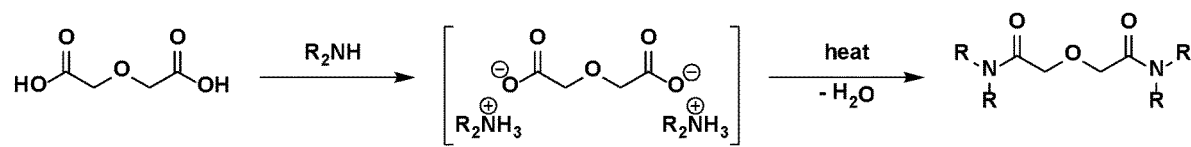
FIG. 3 is a schematic showing an inventive one-pot process for producing a symmetrical DGA compound according to Formula (1).

In the method for producing DGA compounds of Formula (1), a diglycolic acid molecule (A) and a secondary amine (B) are combined to form a salt intermediate (C), followed by heating the salt intermediate (C) to a temperature of 100° C. to 300° C. to form the diglycolamide of Formula (1) in a dehydration process. The reaction scheme is shown in FIG. 3 and in Scheme 1 below, as follows:

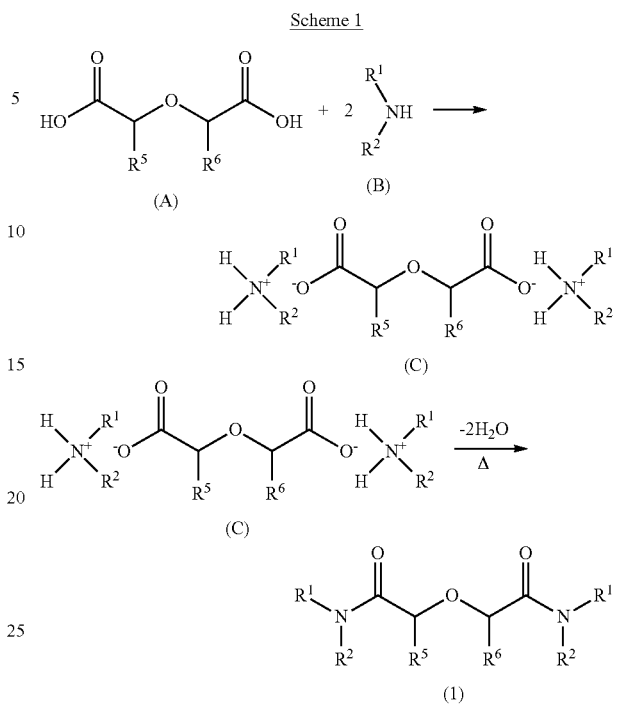

In Scheme 1, $R^1$, $R^2$, $R^5$, and $R^6$ are as defined above under Formula (1), and any of the exemplary selections and combinations of these variables provided under Formula (1) can be made in the reactants (A) and (B) to produce the intermediate (C) and ultimately a compound of Formula (1), which may be any of the compounds of Formula (1) described above. Notably, the diglycolic acid (A) may alternatively be diglycolic acid anhydride, in which case the same intermediate (C) would form under the same conditions. In one embodiment, reactant (A) is combined with two equivalents of reactant (B) in a high boiling point solvent (i.e., a solvent having a boiling point in a range of 100-300° C. or higher) to produce the intermediate (C). The solvent should be non-reactive with the reactants and may be, for example, toluene, a xylene, DMF, ethylene glycol, propylene glycol, decalin, or combination thereof. In another embodiment, reactant (A) is combined with two equivalents of reactant (B) in the absence of a solvent, such as by ball milling. Whether in the presence or absence of a solvent, reactant (A) is combined with two equivalents of reactant (B) under conditions conducive for formation of the intermediate (C).

In some embodiments, reactants (A) and (B) are combined and mixed, either in the presence or absence of a solvent, at ambient temperature and pressure conditions. Ambient temperature is herein considered synonymous with room temperature, which typically corresponds to a temperature in the range of 18-30° C., or more typically 20-25° C. In other embodiments, reactants (A) and (B) are combined and mixed, either in the presence or absence of a solvent, at a mildly elevated temperature above 30° C. and below 100° C. (e.g., 40-80° C.) to further promote formation of the intermediate (C). Once the intermediate (C) is formed, the intermediate (C) is heated (as indicated by the symbol Δ in Scheme 1), either in the presence or absence of a solvent, at an elevated temperature of at least 100° C. and up to 300° C. (or, e.g., a temperature in the range of 100-250° C., 100-200° C., 100-150° C., 150-300° C., 150-250° C., 150-

200° C., 200-300° C., or 250-300° C.) to induce elimination of water (dehydration) to afford a DGA compound of Formula (1). The intermediate (C) may be heated at such temperature for any suitable time period, which may be precisely or at least, for example, 1, 2, 3, 6, 12, 24, 36, or 48 hours, or a time within a range bounded by any two of the foregoing values (e.g., 1-48, 1-24, 3-48, 3-24, 6-48, 6-24, 12-48, or 12-24 hours). The above described process shown in FIG. 3 and Scheme 1 above advantageously eliminates the use of reagents that result in formation of toxic, corrosive, and flammable byproducts. This is a one pot reaction in which the reagents (i.e., diglycolic acid and secondary amine) are mixed, and afterwards, the in situ formed salt is heated above 100° C. to remove water.

In a second aspect, the present disclosure is directed to a lower-cost and more direct method for producing asymmetric or symmetric DGAs of the formula:

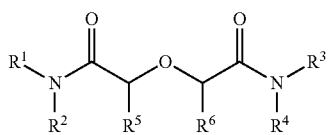
(2)

The variables $R^1$, $R^2$, $R^3$ and $R^4$ in Formula (2) are independently selected from alkyl groups (R) and acyl groups (C(O)R) in which the alkyl groups (R) contain 1-30 carbon atoms and optionally contain an ether or thioether linkage between carbon atoms, as described above. In a first set of embodiments, $R^1$ and $R^2$ are structurally equivalent (the same) to each other, and $R^3$ and $R^4$ are structurally equivalent to each other, but $R^1$ and $R^2$ are structurally different from $R^3$ and $R^4$. In a second set of embodiments, $R^1$ and $R^3$ are structurally equivalent to each other, and $R^2$ and $R^4$ are structurally equivalent to each other, but $R^1$ and $R^3$ are structurally different from $R^2$ and $R^4$. In a third set of embodiments, $R^2$, $R^3$, and $R^4$ are structurally equivalent, but $R^1$ is structurally different from $R^2$, $R^3$, and $R^4$. In a fourth set of embodiments, $R^1$, $R^2$, $R^3$, and $R^4$ are structurally equivalent (the same). In a fifth set of embodiments, $R^1$, $R^2$, $R^3$, and $R^4$ are all different.

In one set of embodiments, $R^1$, $R^2$, $R^3$ and $R^4$ in Formula (2) are independently selected from linear, branched, and/or cyclic alkyl groups (R) containing 1-30 carbon atoms or a number of carbon atoms within a range therein, e.g., 2-30, 3-30, 4-30, 6-30, 8-30, 10-30, 12-30, 1-20, 6-20, 8-20, 10-20, 12-20, 1-12, 6-12, 8-12, 1-6, 2-6, or 3-6 carbon atoms. In one set of embodiments, $R^1$, $R^2$, $R^3$ and/or $R^4$ are alkyl groups composed of only carbon and hydrogen atoms, i.e., without containing any heteroatoms, such as fluorine, oxygen, sulfur, or nitrogen. In another set of embodiments, $R^1$, $R^2$, $R^3$ and/or $R^4$ are alkyl groups containing partial or complete fluorination. In another set of embodiments, one, two, three, or all of $R^1$, $R^2$, $R^3$ and $R^4$ contain an ether or thioether linkage between carbon atoms, which may be in the absence or presence of fluorination of the alkyl group. In some embodiments, $R^1$ is equivalent to (same as) $R^2$ in carbon number, structure, or both. In other embodiments, $R^1$ is different from $R^2$ in carbon number, structure, or both. For example, $R^1$ may be an alkyl group containing 1-3 carbon atoms and $R^2$ may be an alkyl group containing 4-30 carbon atoms. In some embodiments, $R^3$ is equivalent to (same as) $R^4$ in carbon number, structure, or both. In other embodiments, $R^3$ is different from $R^4$ in carbon number, structure, or both. For example, $R^3$ may be an alkyl group containing 1-3 carbon atoms and $R^4$ may be an alkyl group containing 4-30 carbon atoms. In some embodiments, $R^1$ is equivalent to (same as) $R^3$ in carbon number, structure, or both. In other embodiments, $R^1$ is different from $R^3$ in carbon number, structure, or both. For example, $R^1$ may be an alkyl group containing 1-3 carbon atoms and $R^3$ may be an alkyl group containing 4-30 carbon atoms. In some embodiments, $R^2$ is equivalent to (same as) $R^4$ in carbon number, structure, or both. In other embodiments, $R^2$ is different from $R^4$ in carbon number, structure, or both. For example, $R^2$ may be an alkyl group containing 1-3 carbon atoms and $R^4$ may be an alkyl group containing 4-30 carbon atoms. Moreover, any two or more of the above exemplary embodiments may be combined. For example, in some embodiments, $R^1$ and $R^2$ are equivalent to each other, and $R^3$ and $R^4$ are equivalent to each other, but $R^1$ and $R^2$ are different from $R^3$ and $R^4$.

In another set of embodiments, one, two, three, or all of $R^1$, $R^2$, $R^3$ and $R^4$ in Formula (2) are independently selected from C(O)R groups in which R is a linear, branched, and/or cyclic alkyl group (R) containing 1-30 carbon atoms or a number of carbon atoms within a range therein, e.g., 2-30, 3-30, 4-30, 6-30, 8-30, 10-30, 12-30, 1-20, 6-20, 8-20, 10-20, 12-20, 1-12, 6-12, 8-12, 1-6, 2-6, or 3-6 carbon atoms. In one set of embodiments, one, two, three, or all of $R^1$, $R^2$, $R^3$ and $R^4$ are C(O)R groups in which R is selected from alkyl groups composed of only carbon and hydrogen atoms, i.e., without containing any heteroatoms, such as fluorine, oxygen, sulfur, or nitrogen. In another set of embodiments, one, two, three, or all of $R^1$, $R^2$, $R^3$ and $R^4$ are C(O)R groups in which R is selected from alkyl groups containing partial or complete fluorination. In another set of embodiments, one, two, three, or all of $R^1$, $R^2$, $R^3$ and $R^4$ are C(O)R groups in which R contains an ether or thioether linkage between carbon atoms, which may be in the absence or presence of fluorination of the alkyl group (R). In some embodiments, the alkyl group (R) in C(O)R in $R^1$ is equivalent to (same as) the alkyl group (R) in C(O)R in $R^2$ in carbon number, structure, or both. In other embodiments, the alkyl group (R) in C(O)R in $R^1$ is different from the alkyl group (R) in C(O)R in $R^2$ in carbon number, structure, or both. For example, $R^1$ may be a CO(R) group in which R is an alkyl group containing 1-3 carbon atoms and $R^2$ may be a C(O)R group in which R is an alkyl group containing 4-30 carbon atoms. Similarly, in some embodiments, the alkyl group (R) in C(O)R in $R^3$ is equivalent to (same as) the alkyl group (R) in C(O)R in $R^4$ in carbon number, structure, or both. In other embodiments, the alkyl group (R) in C(O)R in $R^3$ is different from the alkyl group (R) in C(O)R in $R^4$ in carbon number, structure, or both. For example, $R^3$ may be a CO(R) group in which R is an alkyl group containing 1-3 carbon atoms and $R^4$ may be a C(O)R group in which R is an alkyl group containing 4-30 carbon atoms. In other embodiments, the alkyl group (R) in C(O)R in $R^1$ is equivalent to (same as) the alkyl group (R) in C(O)R in $R^3$ in carbon number, structure, or both. In other embodiments, the alkyl group (R) in C(O)R in $R^1$ is different from the alkyl group (R) in C(O)R in $R^3$ in carbon number, structure, or both. For example, $R^1$ may be a CO(R) group in which R is an alkyl group containing 1-3 carbon atoms and $R^3$ may be a C(O)R group in which R is an alkyl group containing 4-30 carbon atoms. Similarly, in other embodiments, the alkyl group (R) in C(O)R in $R^2$ is equivalent to (same as) the alkyl group (R) in C(O)R in $R^4$ in carbon number, structure, or both. In other embodiments, the alkyl group (R) in C(O)R in $R^2$ is different from the alkyl group (R) in C(O)R in $R^4$ in carbon number, structure, or both. For example, $R^2$ may be a CO(R) group in which R is an alkyl group containing 1-3 carbon atoms and $R^4$ may be a C(O)R group in which R is an alkyl group containing 4-30 carbon atoms. Moreover, any two or more of the above exemplary embodiments may be combined. For example, in some embodiments, the alkyl group (R) in C(O)R in $R^1$ and $R^2$ are equivalent to each other, and the alkyl group (R) in C(O)R in $R^3$ and $R^4$ are equivalent to each other, but $R^1$ and $R^2$ are different from $R^3$ and $R^4$.

In another set of embodiments, a portion of $R^1$, $R^2$, $R^3$ and $R^4$ groups in Formula (2) are independently selected from linear, branched, and/or cyclic alkyl groups (R) containing 1-30 carbon atoms, and a portion of $R^1$, $R^2$, $R^3$ and $R^4$ groups are independently selected from C(O)R groups, thereby resulting in a compound of Formula (2) containing a mixture of R and C(O)R groups. For example, $R^1$ and $R^3$ may be independently selected as same or different R groups, and $R^2$ and $R^4$ may be independently selected as same or different C(O)R groups. Alternatively, for example, $R^1$ and $R^2$ may be independently selected as same or different R groups, and $R^3$ and $R^4$ may be independently selected as same or different C(O)R groups. Alternatively, for example, $R^1$ may be selected as an R group, and $R^2$, $R^3$, and $R^4$ may be independently selected as C(O)R groups. Alternatively, for example, $R^1$ may be selected as a C(O)R group, and $R^2$, $R^3$, and $R^4$ may be independently selected as R groups.

Moreover, $R^1$ and $R^2$ in Formula (2) are optionally interconnected to form a ring, and/or $R^3$ and $R^4$ are optionally interconnected to form a ring. The ring is typically a five- or six-membered ring. For example, $R^1$ and $R^2$ can each be selected as ethyl groups followed by interconnection at the terminal carbon atom of each ethyl group, thus resulting in formation of a five-membered ring (specifically, a pyrrolidinyl ring). Alternatively, one or both of $R^1$ and $R^2$ can be selected as a C(O)R group, thereby resulting in a lactam or succinimide ring. $R^3$ and $R^4$ may be analogously interconnected as provided above for $R^1$ and $R^2$. In the case of two rings being present, the rings may be the same or different in size and/or structure.

The variables $R^5$ and $R^6$ in Formula (2) are independently selected from hydrogen atom and alkyl groups (R') containing 1-3 carbon atoms. In some embodiments, precisely or at least one of $R^5$ and $R^6$ is a hydrogen atom, or $R^5$ and $R^6$ may both be hydrogen atoms. In other embodiments, precisely or at least one of $R^5$ and $R^6$ is an alkyl group (R') containing 1-3 carbon atoms, or $R^5$ and $R^6$ may both be R'. In the case where $R^5$ and $R^6$ are both alkyl groups (R') containing 1-3 carbon atoms, $R^5$ and $R^6$ may be the same or different. In some embodiments, precisely or at least one of $R^5$ and $R^6$ is a methyl group, or $R^5$ and $R^6$ may both be methyl groups. In some embodiments, one of $R^5$ and $R^6$ is an alkyl group and one of $R^5$ and $R^6$ is a hydrogen atom. Notably, any of the above selections and combinations provided for $R^5$ and $R^6$ groups can be combined with any of the selections and combinations provided earlier above for $R^1$, $R^2$, $R^3$ and $R^4$ groups.

In a first step in the method for producing DGA compounds of Formula (2), a glycolic acid molecule (D) and a first secondary amine (B) are combined to form a salt intermediate (E), followed by heating the salt intermediate (E) to a temperature of 100° C. to 300° C. to form a glycolamide (F) in a dehydration process. The reaction scheme for the first step is shown in Scheme 2 below, as follows:

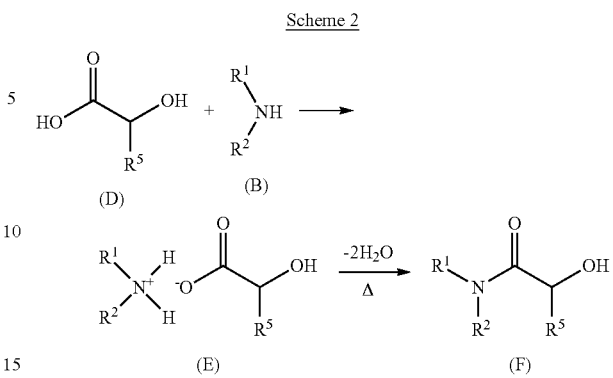

In Scheme 2, $R^1$, $R^2$, and $R^5$ are as defined above under Formula (2), and any of the exemplary selections and combinations of these variables provided under Formula (2) can be made in the reactants (D) and (B) to produce the intermediate (E) and ultimately a first reactant (F). Notably, the glycolic acid molecule (D) may alternatively be a diglycolic acid anhydride, in which case the same intermediate (E) would form under the same conditions. In one embodiment, reactant (D) is combined with one equivalent of reactant (B) in a high boiling point solvent (i.e., a solvent having a boiling point in a range of 100-300° C. or higher) to produce the intermediate (E). The solvent should be non-reactive with the reactants and may be, for example, toluene, a xylene, DMF, ethylene glycol, propylene glycol, decalin, or combination thereof. In another embodiment, reactant (D) is combined with an equivalent of reactant (B) in the absence of a solvent, such as by ball milling. Whether in the presence or absence of a solvent, reactant (D) is combined with an equivalent of reactant (B) under conditions conducive for formation of the intermediate (E). In some embodiments, reactants (D) and (B) are combined and mixed, either in the presence or absence of a solvent, at ambient temperature and pressure conditions. Ambient temperature is herein considered synonymous with room temperature, which typically corresponds to a temperature in the range of 18-30° C., or more typically 20-25° C. In other embodiments, reactants (D) and (B) are combined and mixed, either in the presence or absence of a solvent, at a mildly elevated temperature above 30° C. and below 100° C. (e.g., 40-80° C.) to further promote formation of the intermediate (D). Once the intermediate (E) is formed, the intermediate (E) is heated (as indicated by the symbol Δ in Scheme 2), either in the presence or absence of a solvent, at an elevated temperature of at least 100° C. and up to 300° C. (or, e.g., a temperature in the range of 100-250° C., 100-200° C., 100-150° C., 150-300° C., 150-250° C., 150-200° C., 200-300° C., or 250-300° C.) to induce elimination of water (dehydration) to afford the first reactant (F) shown in Formula (2). The intermediate (E) may be heated at such temperature for any suitable time period, which may be precisely or at least, for example, 1, 2, 3, 6, 12, 24, 36, or 48 hours, or a time within a range bounded by any two of the foregoing values (e.g., 1-48, 1-24, 3-48, 3-24, 6-48, 6-24, 12-48, or 12-24 hours).

In a second step in the method for producing DGA compounds of Formula (2), a molecule (G) is reacted with a second secondary amine (B') to form a second reactant (H). The reaction scheme for the second step is shown as follows in Scheme 3 below:

Scheme 3

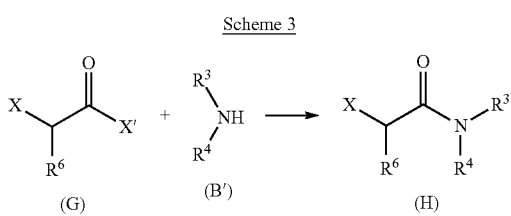

In Scheme 3, $R^3$, $R^4$, and $R^6$ are as defined above under Formula (2), and any of the exemplary selections and combinations of these variables provided under Formula (2) can be made in the reactants (G) and (B') to produce the second reactant (H). The variable X is a halogen atom or pseudo-halogen atom, and X' is a halogen atom. Some examples of halogen atoms (X) include chloride, bromide, and iodide. Some examples of pseudo-halogens include triflate, tosylate, mesylate, and nosylate. In one embodiment, reactant (G) is combined with an equivalent of reactant (B') in a solvent (e.g., an ether solvent, such as THF or diethyl ether), or any solvent described earlier above, to produce the second reactant (H). In another embodiment, reactant (G) is combined with an equivalent of reactant (B') in the absence of a solvent, such as by ball milling. Whether in the presence or absence of a solvent, reactant (G) is combined with an equivalent of reactant (B') under conditions conducive for formation of the second reactant (H). In some embodiments, reactants (G) and (B') are combined and mixed, either in the presence or absence of a solvent, at ambient temperature and pressure conditions. Ambient temperature is herein considered synonymous with room temperature, which typically corresponds to a temperature in the range of 18-30° C., or more typically 20-25° C. In some embodiments, the reaction system is cooled during production of the second reactant (H).

In a third step in the method for producing DGA compounds of Formula (2), the first reactant (F) is reacted with the second reactant (H) in the presence of a base of sufficient strength to deprotonate first reactant (F) to form a compound of Formula (2), which may be any of the compounds of Formula (2) described earlier above. The reaction scheme for the third step is shown as follows in Scheme 4 below:

Scheme 4

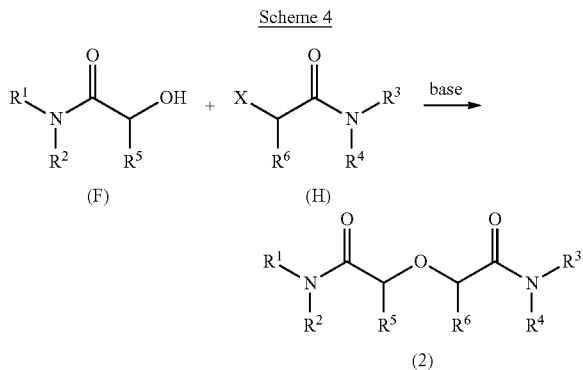

Figure 4:
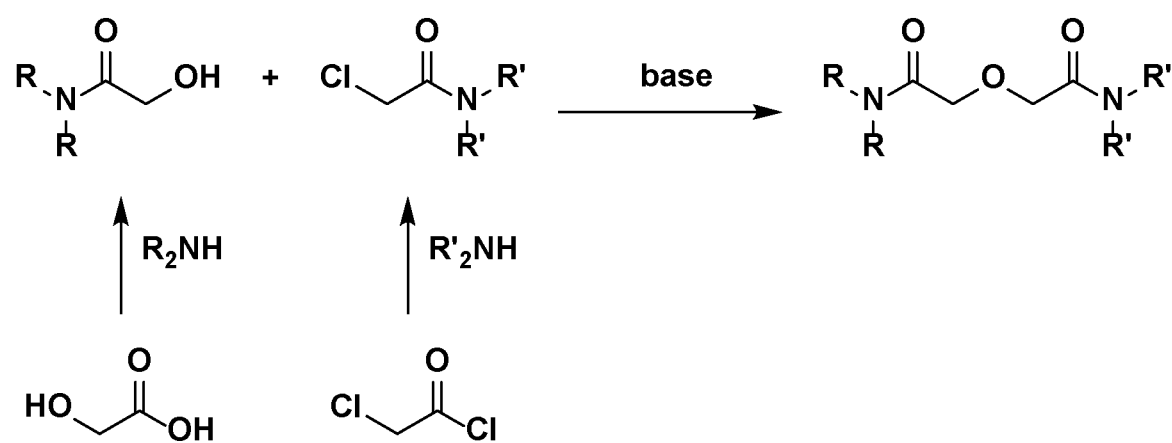
FIG. 4 is a schematic showing an inventive three-step convergent process for producing a symmetric or asymmetric DGA compound according to Formula (2).

An exemplary process for conducting the full three-step convergent reaction scheme is shown in FIG. 4. In one embodiment, reactant (F) is combined with an equivalent of reactant (H) in a solvent (e.g., an ether solvent, such as THF or diethyl ether) or any solvent described earlier above, to produce the final product (2). In another embodiment, reactant (F) is combined with an equivalent of reactant (H) in the absence of a solvent, such as by ball milling. Whether in the presence or absence of a solvent, reactant (F) is combined with an equivalent of reactant (H) under conditions conducive for formation of the final product (2). In some embodiments, reactants (F) and (H) are combined and mixed, either in the presence or absence of a solvent, at ambient temperature and pressure conditions. Ambient temperature is herein considered synonymous with room temperature, which typically corresponds to a temperature in the range of 18-30° C., or more typically 20-25° C. In some embodiments, the reaction system is cooled during production of the final product (2) in step (iii).

The base in Scheme 4, i.e., step (iii), may be any base capable of deprotonating the hydroxy group in the first reactant (F). The base may be selected from, for example, alkali hydrides, alkali hydroxides, alkali alkoxides, alkali dialkylamides, alkali bis(trimethylsilyl)amides, and tertiary amines. Some examples of alkali hydrides include NaH and LiH. Some examples of alkali hydroxides include LiOH, NaOH, and KOH. Some examples of alkali alkoxides include lithium methoxide, sodium methoxide, sodium ethoxide, sodium isopropoxide, sodium butoxide, sodium t-butoxide, potassium methoxide, potassium ethoxide, potassium isopropoxide, potassium butoxide, and potassium t-butoxide. Some examples of alkali dialkylamides include lithium diisopropylamide, sodium diisopropylamide, and lithium diisobutylamide. Some examples of alkali bis(trimethylsilyl)amides include sodium bis(trimethylsilyl)amide, lithium bis(trimethylsilyl)amide, and potassium bis(trimethylsilyl)amide. Some examples of tertiary amines include triethylamine, triisopropylamine, and triisobutylamine. Any combination of the above bases may also be used, such as an alkali hydroxide or alkoxide and a tertiary amine.

In a third aspect, the present disclosure is directed to a lower-cost and more direct method for producing cyclic DGAs of the formula:

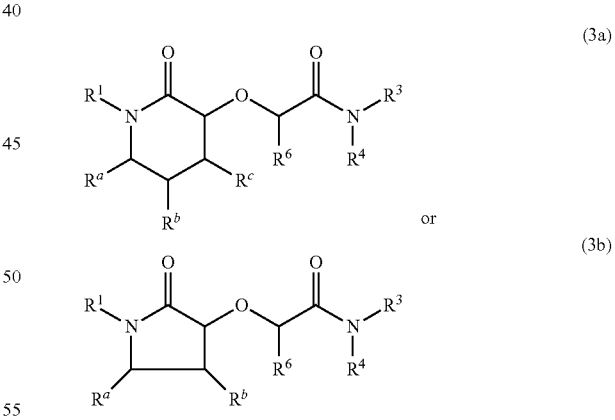

The variables $R^1$, $R^3$ and $R^4$ in Formula (3a) or (3b) are independently selected from alkyl groups (R) and acyl groups (C(O)R) in which the alkyl groups (R) contain 1-30 carbon atoms and optionally contain an ether or thioether linkage between carbon atoms, as described above. In a one set of embodiments, $R^1$, $R^3$ and $R^4$ are structurally equivalent (the same) to each other. In another set of embodiments, $R^1$ is structurally different from $R^3$ and $R^4$, and $R^3$ and $R^4$ are structurally the same or different from each other.

In one set of embodiments, $R^1$, $R^3$ and $R^4$ in Formula (3a) or (3b) are independently selected from linear, branched, and/or cyclic alkyl groups (R) containing 1-30 carbon atoms or a number of carbon atoms within a range therein, e.g., 2-30, 3-30, 4-30, 6-30, 8-30, 10-30, 12-30, 1-20, 6-20, 8-20, 10-20, 12-20, 1-12, 6-12, 8-12, 1-6, 2-6, or 3-6 carbon atoms. In one set of embodiments, $R^1$, $R^3$ and $R^4$ are alkyl groups composed of only carbon and hydrogen atoms, i.e., without containing any heteroatoms, such as fluorine, oxygen, sulfur, or nitrogen. In another set of embodiments, $R^1$, $R^3$ and $R^4$ are alkyl groups containing partial or complete fluorination. In another set of embodiments, one, two, or all of $R^1$, $R^3$ and $R^4$ contain an ether or thioether linkage between carbon atoms, which may be in the absence or presence of fluorination of the alkyl group. In some embodiments, $R^1$ is equivalent to (same as) $R^3$ or $R^4$ in carbon number, structure, or both. In other embodiments, $R^1$ is different from $R^3$ or $R^4$ in carbon number, structure, or both. For example, $R^1$ may be an alkyl group containing 1-3 carbon atoms and $R^3$ or $R^4$ may be an alkyl group containing 4-30 carbon atoms, vice-versa. In some embodiments, $R^3$ is equivalent to (same as) $R^4$ in carbon number, structure, or both. In other embodiments, $R^3$ is different from $R^4$ in carbon number, structure, or both. For example, $R^3$ may be an alkyl group containing 1-3 carbon atoms and $R^4$ may be an alkyl group containing 4-30 carbon atoms.

In another set of embodiments, one, two, or all of $R^1$, $R^3$ and $R^4$ in Formula (3a) or (3b) are independently selected from C(O)R groups in which R is a linear, branched, and/or cyclic alkyl group (R) containing 1-30 carbon atoms or a number of carbon atoms within a range therein, e.g., 2-30, 3-30, 4-30, 6-30, 8-30, 10-30, 12-30, 1-20, 6-20, 8-20, 10-20, 12-20, 1-12, 6-12, 8-12, 1-6, 2-6, or 3-6 carbon atoms. In one set of embodiments, one, two, or all of $R^1$, $R^3$ and $R^4$ are C(O)R groups in which R is selected from alkyl groups composed of only carbon and hydrogen atoms, i.e., without containing any heteroatoms, such as fluorine, oxygen, sulfur, or nitrogen. In another set of embodiments, one, two, or all of $R^1$, $R^3$ and $R^4$ are C(O)R groups in which R is selected from alkyl groups containing partial or complete fluorination. In another set of embodiments, one, two, or all of $R^1$, $R^3$ and $R^4$ are C(O)R groups in which R contains an ether or thioether linkage between carbon atoms, which may be in the absence or presence of fluorination of the alkyl group (R). In some embodiments, the alkyl group (R) in C(O)R in $R^1$ is equivalent to (same as) the alkyl group (R) in C(O)R in $R^2$ or $R^3$ in carbon number, structure, or both. In other embodiments, the alkyl group (R) in C(O)R in $R^1$ is different from the alkyl group (R) in C(O)R in $R^2$ or $R^3$ in carbon number, structure, or both. For example, $R^1$ may be a CO(R) group in which R is an alkyl group containing 1-3 carbon atoms and $R^1$ and/or $R^3$ may be a C(O)R group in which R is an alkyl group containing 4-30 carbon atoms. Similarly, in some embodiments, the alkyl group (R) in C(O)R in $R^3$ is equivalent to (same as) the alkyl group (R) in C(O)R in $R^4$ in carbon number, structure, or both. In other embodiments, the alkyl group (R) in C(O)R in $R^3$ is different from the alkyl group (R) in C(O)R in $R^4$ in carbon number, structure, or both. For example, $R^3$ may be a CO(R) group in which R is an alkyl group containing 1-3 carbon atoms and $R^4$ may be a C(O)R group in which R is an alkyl group containing 4-30 carbon atoms.

Moreover, $R^3$ and $R^4$ in Formula (3a) or (3b) are optionally interconnected to form a ring, and/or $R^4$ and $R^6$ are optionally interconnected to form a ring. The ring is typically a five- or six-membered ring. For example, $R^3$ and $R^4$ can each be selected as ethyl groups followed by interconnection at the terminal carbon atom of each ethyl group, thus resulting in formation of a five-membered ring (specifically, a pyrrolidinyl ring). Alternatively, one or both of $R^3$ and $R^4$ can be selected as a C(O)R group, thereby resulting in a lactam or succinimide ring. $R^4$ and $R^6$ may be analogously interconnected as provided above for $R^3$ and $R^4$. In the case of two rings being present, the rings may be the same or different in size and/or structure.

The variable $R^6$ in Formula (3a) or (3b) is selected from hydrogen atom and alkyl groups (R') containing 1-3 carbon atoms. In some embodiments, $R^6$ is a hydrogen atom. In other embodiments, $R^6$ is an alkyl group (R') containing 1-3 carbon atoms. In some embodiments, $R^6$ is a methyl group. Notably, any of the above selections provided above for $R^6$ groups can be combined with any of the selections and combinations provided earlier above for $R^1$, $R^3$, and $R^4$ groups.

The variables $R^a$, $R^b$, and $R^c$ in Formula (3a) or (3b) are independently selected from hydrogen atom, alkyl groups (R), acyl groups (C(O)R), amide groups (C(O)NR$_2$), alkoxide groups (OR), and amine groups (NR$_2$) in which the alkyl groups (R) independently contain 1-30 carbon atoms and optionally contain an ether or thioether linkage between carbon atoms. In a first set of embodiments, one, two, or all of $R^a$, $R^b$, and $R^c$ are hydrogen atoms. In a second set of embodiments, one, two, or all of $R^a$, $R^b$, and $R^c$ are alkyl groups. In a third set of embodiments, one, two, or all of $R^a$, $R^b$, and $R^c$ are acyl groups. In a fourth set of embodiments, one, two, or all of $R^a$, $R^b$, and $R^c$ are amide groups. In a fifth set of embodiments, one, two, or all of $R^a$, $R^b$, and $R^c$ are alkoxide groups. In a sixth set of embodiments, one, two, or all of $R^a$, $R^b$, and $R^c$ are amine groups. Any two or more of the foregoing exemplary embodiments may be combined.

In the method for producing cyclic DGA compounds of Formula (3a) or (3b), a first reactant (J or J') is reacted with a second reactant (H) in the presence of a base of sufficient strength to deprotonate the first reactant (J or J') to form a compound of Formula (3a) or (3b), which may be any of the cyclic compounds of Formula (3a) or (3b) described earlier above. The reaction scheme for the process is shown in Scheme 5 below:

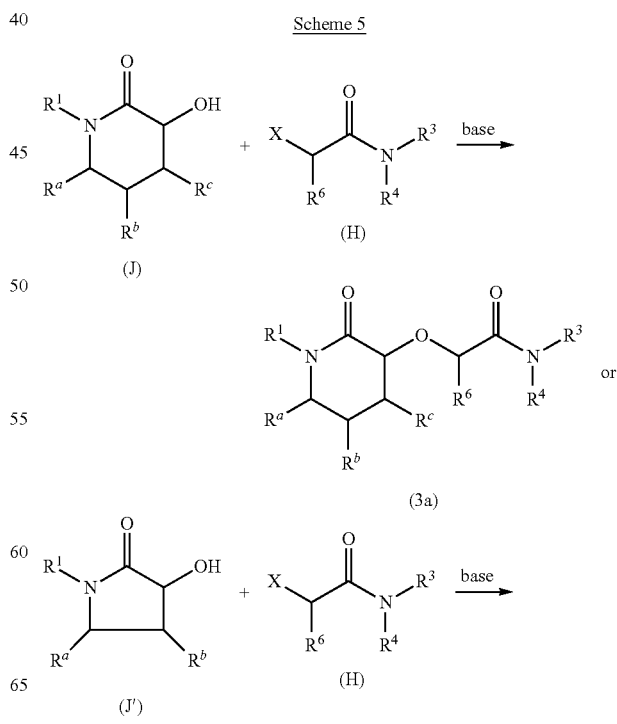

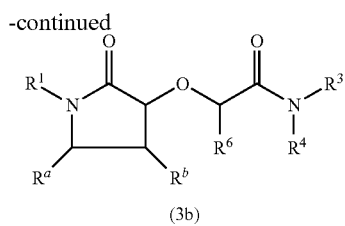

(3b)

In one embodiment, reactant (J) or (J') is combined with an equivalent of reactant (H) in a solvent (e.g., an ether solvent, such as THF or diethyl ether) or any solvent described earlier above, to produce the final product (3a) or (3b). In another embodiment, reactant (J) or (J') is combined with an equivalent of reactant (H) in the absence of a solvent, such as by ball milling. Whether in the presence or absence of a solvent, reactant (J) or (J') is combined with an equivalent of reactant (H) under conditions conducive for formation of the final product (3a) or (3b). In some embodiments, reactants (J) or (J') and (H) are combined and mixed, either in the presence or absence of a solvent, at ambient temperature and pressure conditions. Ambient temperature is herein considered synonymous with room temperature, which typically corresponds to a temperature in the range of 18-30° C., or more typically 20-25° C. In some embodiments, the reaction system is cooled during production of the final product (3a) or (3b).

The base in Scheme 5 may be any base capable of deprotonating the hydroxy group in the first reactant (J) or (J'). The base may be selected from, for example, alkali hydrides, alkali hydroxides, alkali alkoxides, alkali dialkylamides, alkali bis(trimethylsilyl)amides, and tertiary amines. Some examples of alkali hydrides include NaH and LiH. Some examples of alkali hydroxides include LiOH, NaOH, and KOH. Some examples of alkali alkoxides include lithium methoxide, sodium methoxide, sodium ethoxide, sodium isopropoxide, sodium butoxide, sodium t-butoxide, potassium methoxide, potassium ethoxide, potassium isopropoxide, potassium butoxide, and potassium t-butoxide. Some examples of alkali dialkylamides include lithium diisopropylamide, sodium diisopropylamide, and lithium diisobutylamide. Some examples of alkali bis(trimethylsilyl)amides include sodium bis(trimethylsilyl)amide, lithium bis(trimethylsilyl)amide, and potassium bis(trimethylsilyl)amide. Some examples of tertiary amines include triethylamine, triisopropylamine, and triisobutylamine. Any combination of the above bases may also be used, such as an alkali hydroxide or alkoxide and a tertiary amine.

Using the above methods, a diverse number of DGA compounds can be prepared. For example, the compounds may be within a sub-class of Formula (1) or Formula (2) in which $R^1$ and $R^2$ (or $R^1$, $R^2$, $R^3$, and $R^4$) are all alkyl groups and within the following sub-formula:

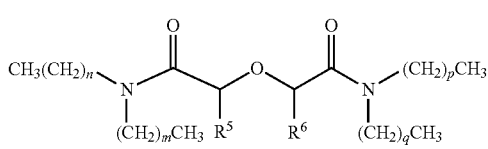

(1a)

wherein m, n, p, and q are each independently an integer of 0-20, provided that the sum of m, n, p, and q is at least 8, and where $R^5$ and $R^6$ are as defined above. In some embodiments, m, n, p, and q are the same, such as m, n, p, and q all being 3, 4, 5, 6, 7, 8, 9, 10, 11, 12, 13, 14, 15, 16, 17, 18, or 19. In other embodiments, m, n, p, and q are not all the same, such as m and q being 0 and n and p each being 4, 5, 6, 7, 8, 9, 10, 11, 12, 13, 14, 15, 16, 17, 18, or 19; or, as another example, m and q being 1 or 2 and n and p each being 3, 4, 5, 6, 7, 8, 9, 10, 11, 12, 13, 14, 15, 16, 17, 18, or 19. Moreover, any one or more hydrogen atoms in methylene groups in Formula (1a) may optionally be replaced with a methyl, ethyl, n-propyl, or isopropyl group, to result in a branched hydrocarbon group, provided that the branched hydrocarbon group contains up to 20 carbon atoms, as provided in Formula (1).

Some examples of specific compounds under Formula (1) or (2) are provided as follows:

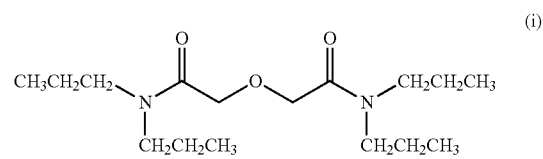

(i)

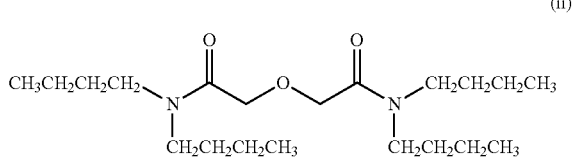

(ii)

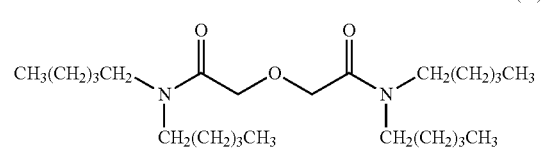

(iii)

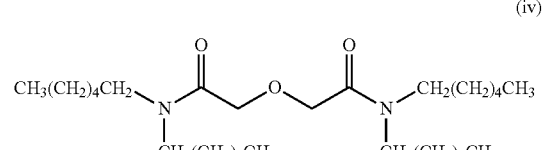

(iv)

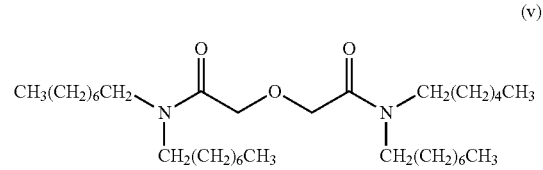

(v)

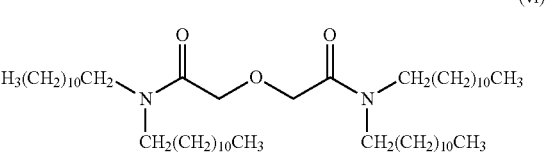

(vi)

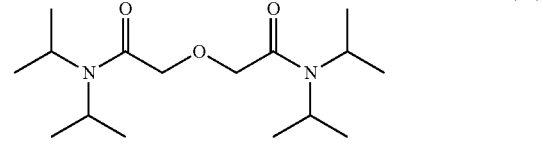

(vii)

-continued

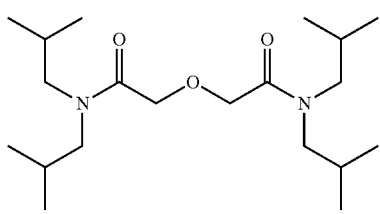
(viii)

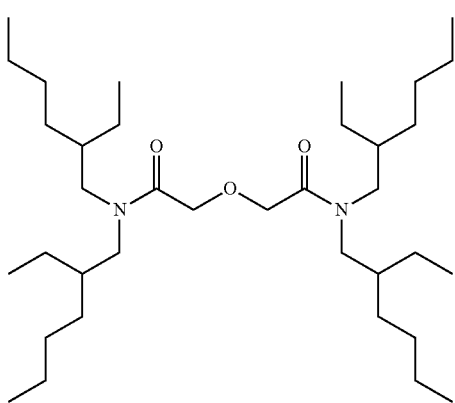
(ix)

Some examples of specific compounds under Formula (2) in which not all alkyl groups corresponding to $R^1$, $R^2$, $R^3$, and $R^4$ are the same are provided as follows:

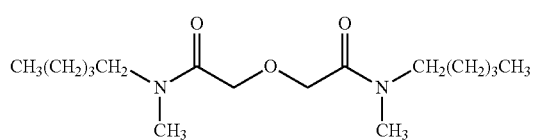
(x)

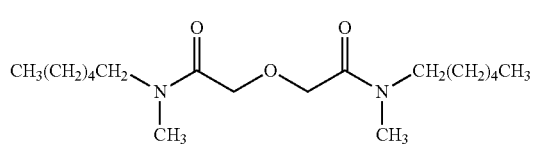
(xi)

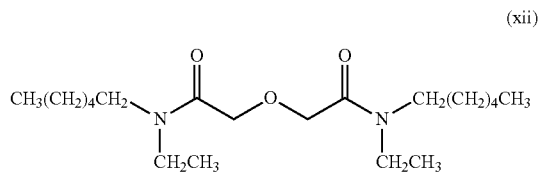
(xii)

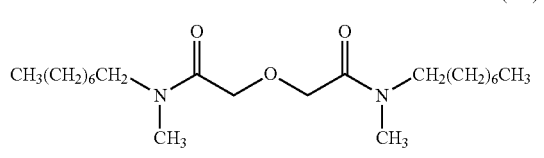
(xiii)

-continued

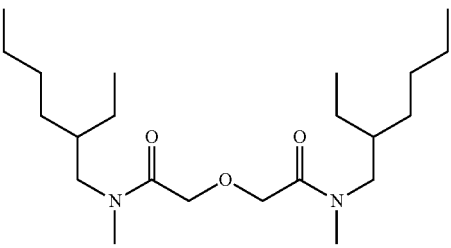
(xiv)

In some embodiments of Formula (1) or (2), a first condition applies in which at least one (e.g., one, two, three, or all) of $R^1$, $R^2$, $R^3$, and $R^4$ is a distal branched alkyl group constructed of a linear alkyl backbone having at least four, five, six, seven, eight, nine, ten, eleven, or twelve carbon atoms with an alpha carbon atom of the linear alkyl backbone attached to a nitrogen atom shown in Formula (1) or (2), and the linear alkyl backbone contains a substituting hydrocarbon group (which may be an alkyl group) at a gamma carbon or higher positioned carbon on the linear alkyl backbone. The substituting hydrocarbon group can be any of the hydrocarbon groups described above containing at least one or two carbon atoms, provided that the total number of carbon atoms in the distal branched alkyl group is up to 30 carbon atoms. In particular embodiments, one or more of the substituting hydrocarbon groups contain 1-6 carbon atoms, such as those selected from methyl, ethyl, n-propyl, isopropyl, n-butyl, isobutyl, sec-butyl, t-butyl, cyclopentyl, cyclohexyl, and phenyl groups. The linear alkyl backbone may be depicted as follows, with alpha, beta, gamma, delta, and epsilon positions denoted:

—(CH$_2$)$_\alpha$(CH$_2$)$_\beta$(CH$_2$)$_\gamma$(CH$_2$)$_\delta$(CH$_2$)$_\epsilon$(CH$_2$)$_n$(CH$_3$), wherein n is 0 or a number of 1 or greater. In some embodiments, the distal branched alkyl group contains precisely or at least one substituting hydrocarbon group located at a gamma carbon, delta carbon, epsilon carbon, or higher carbon position (e.g., zeta, eta, theta, iota, or kappa) of the linear alkyl backbone. In other embodiments, the distal branched alkyl group contains at least two (or more) substituting hydrocarbon groups independently located at a gamma carbon, delta carbon, epsilon carbon, or higher carbon position (e.g., zeta, eta, theta, iota, or kappa) or combination of such positions of the linear alkyl backbone.

Some examples of distal branched alkyl groups according to the first condition include:

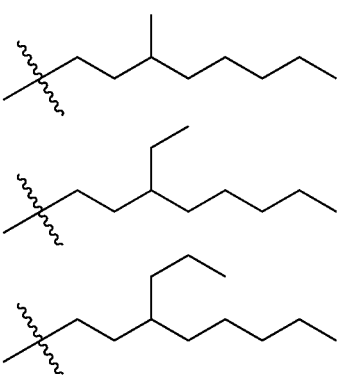

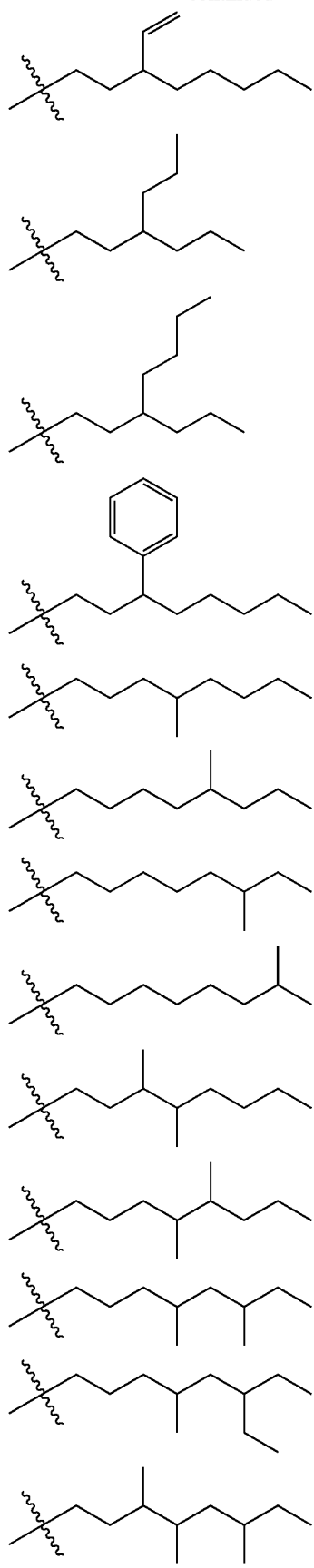
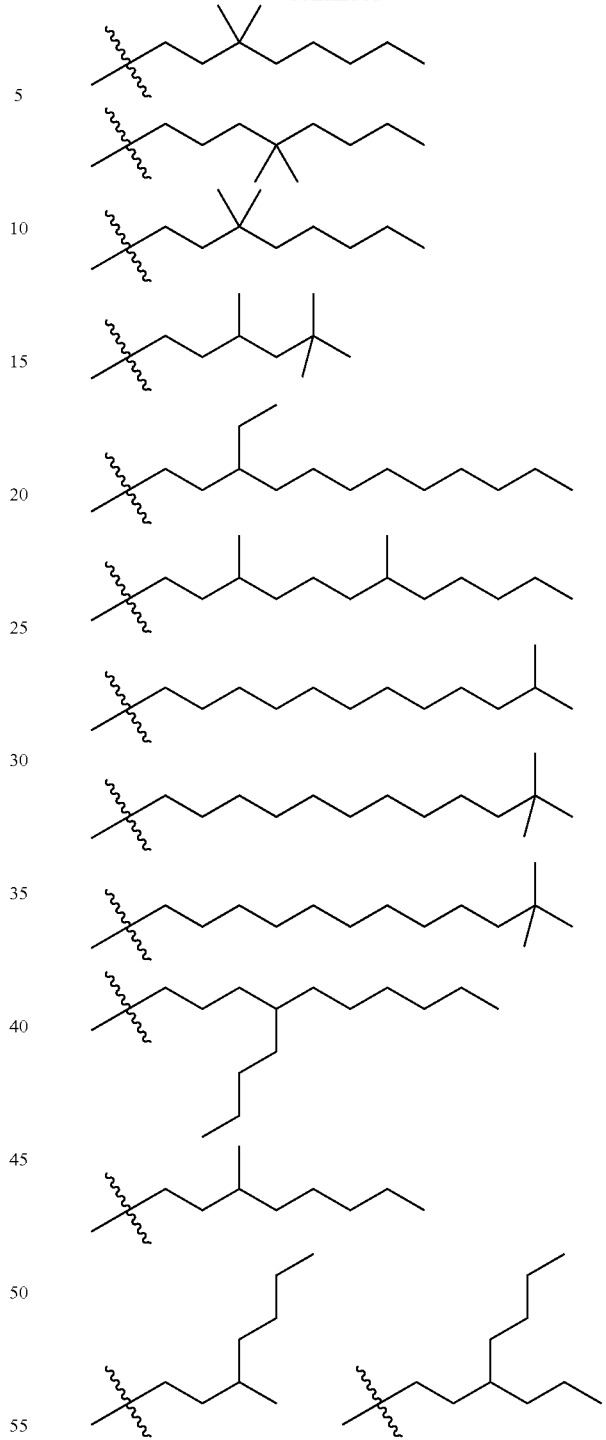

In some embodiments of Formula (2), a second condition applies in which $R^1$ and $R^2$ are equivalent and $R^3$ and $R^4$ are separately equivalent, while $R^1$ and $R^2$ are different from $R^3$ and $R^4$, to result in an asymmetrical compound of Formula (2). In some embodiments, $R^1$ and $R^2$ are equivalent hydrocarbon groups (or more particularly, alkyl groups) containing 1-3 carbon atoms, and $R^3$ and $R^4$ are separately equivalent hydrocarbon groups containing 4-30, 6-30, 8-30, 10-30, 12-30, 4-20, 6-20, 8-20, 10-20, or 12-20 carbon atoms, wherein all such hydrocarbon groups have been described above. For example, $R^1$ and $R^2$ may both be methyl or ethyl and $R^3$ and $R^4$ may both be the same $C_3$-$C_{30}$, $C_4$-$C_{30}$, $C_5$-$C_{30}$, $C_6$-$C_{30}$, $C_7$-$C_{30}$, or $C_8$-$C_{30}$, linear, branched, or cyclic alkyl group, as described above, such as n-propyl, isopropyl, cyclopropyl, n-butyl, sec-butyl, isobutyl, t-butyl, cyclobutyl, n-pentyl, isopentyl, n-hexyl, isohexyl, cyclohexyl, n-octyl, isooctyl, n-decyl, n-undecyl, n-dodecyl, n-tetradecyl, n-hexadecyl, or larger group with or without substitution with one or more hydrocarbon groups (R) as described above. Alternatively, only one of $R^1$, $R^2$, $R^3$, and $R^4$ is different to result in an asymmetrical compound. For example, $R^1$ may be methyl or ethyl and $R^2$, $R^3$, and $R^4$ may all be the same $C_3$-$C_{30}$, $C_4$-$C_{30}$, $C_5$-$C_{30}$, $C_6$-$C_{30}$, $C_7$-$C_{30}$, or $C_8$-$C_{30}$, linear, branched, or cyclic alkyl group, as described above, such as n-propyl, isopropyl, cyclopropyl, n-butyl, sec-butyl, isobutyl, t-butyl, cyclobutyl, n-pentyl, isopentyl, n-hexyl, isohexyl, cyclohexyl, n-octyl, isooctyl, n-decyl, n-undecyl, n-dodecyl, n-tetradecyl, n-hexadecyl, or larger group with or without substitution with one or more hydrocarbon groups (R) as described above. Any of the alkyl groups described above may or may not contain fluorine substitution and/or an ether or thioether linkage connecting between carbon atoms.

In some embodiments, DGA compounds within the scope of Formula (2) contain one or two rings resulting from interconnection of $R^1$ and $R^2$ and/or $R^3$ and $R^4$. Some examples of DGA compounds within the scope of Formula (2) in which $R^1$ and $R^2$ and/or $R^3$ and $R^4$ are interconnected include:

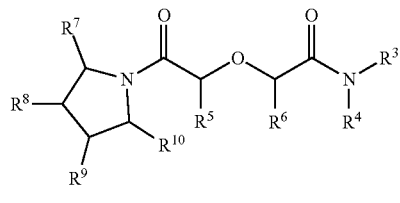

(xv)

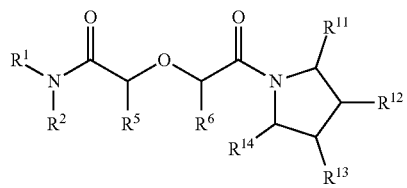

(xvi)

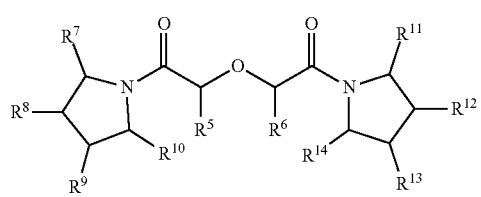

(xvii)

In the above structures (xv), (xvi), and (xvii), $R^7$, $R^8$, $R^9$, $R^{10}$, $R^{11}$, $R^{12}$, $R^{13}$, and $R^{14}$ are independently selected from hydrogen atom (H) and hydrocarbon groups (R) described earlier above, provided that at least one of $R^7$, $R^8$, $R^9$, $R^{10}$, $R^{11}$, $R^{12}$, $R^{13}$, and $R^{14}$ is a hydrocarbon group (R) containing 1-30 carbon atoms. In some embodiments, at least one of $R^7$, $R^8$, $R^9$, $R^{10}$, $R^{11}$, $R^{12}$, $R^{13}$, and $R^{14}$ is an alkyl group containing 1-30 carbon atoms. In some embodiments, at least one of $R^7$, $R^8$, $R^9$, $R^{10}$, $R^{11}$, $R^{12}$, $R^{13}$, and $R^{14}$ is a methyl, ethyl, n-propyl, or isopropyl group. In some embodiments, at least one of $R^7$, $R^8$, $R^9$, $R^{10}$, $R^{11}$, $R^{12}$, $R^{13}$, and $R^{14}$ is a hydrocarbon group (or more particularly, an alkyl group) containing 4-30, 6-30, 8-30, 10-30, 12-30, 4-20, 6-20, 8-20, 10-20, or 12-20 carbon atoms. In particular embodiments, $R^9$ and/or $R^{13}$ is a hydrocarbon group, or more particularly an alkyl group, containing 1-30 carbon atoms or any of the particular sub-ranges of carbon atoms provided above.

Some examples of cyclic DGA compounds within the scope of Formula (3a) or (3b) include:

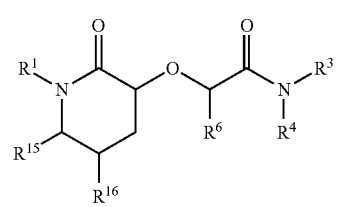

(xviii)

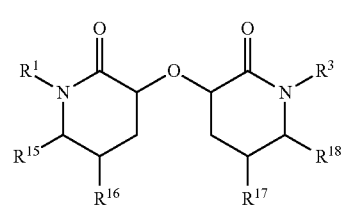

(xix)

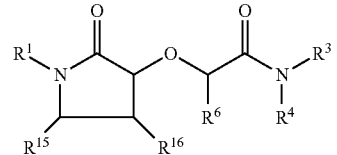

(xx)

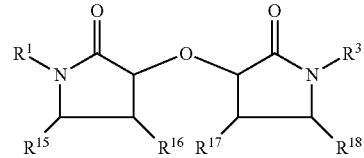

(xxi)

In the above structures (xviii), (xix), (xx), and (xxi), $R^{15}$, $R^{16}$, $R^{17}$, and $R^{18}$ are independently selected from hydrogen atom (H) and hydrocarbon groups (R) described earlier above. In some embodiments, at least one, two, three, or all of $R^{15}$, $R^{16}$, $R^{17}$, and $R^{18}$ are hydrogen atoms. In other embodiments, precisely or at least one of $R^{15}$, $R^{16}$, $R^{17}$, and $R^{18}$ is a hydrocarbon group (R) or more particularly a linear, branched, or cyclic alkyl group containing precisely or at least 3, 4, 5, 6, 7, 8, 9, 10, 11, or 12 and up to 14, 16, 18, 20, 22, 24, 26, 28, or 30 carbon atoms, or an alkyl group containing a number of carbon atoms within a range bounded by any two of the foregoing values (e.g., 3-30, 4-30, 6-30, 8-30, 10-30, 12-30, 3-20, 4-20, 6-20, 8-20, 10-20, or 12-20 carbon atoms). In typical embodiments, at least one (or both) of $R^1$ and $R^3$ in the above structures (1c-1), (1c-2), (1c-3), and (1c-4) is a linear, branched, or cyclic alkyl group containing precisely or at least 3, 4, 5, 6, 7, 8, 9, 10, 11, or 12 and up to 14, 16, 18, 20, 22, 24, 26, 28, or 30 carbon atoms, or an alkyl group containing a number of carbon atoms within a range bounded by any two of the foregoing values (e.g., 3-30, 4-30, 6-30, 8-30, 10-30, 12-30, 3-20, 4-20, 6-20, 8-20, 10-20, or 12-20 carbon atoms). In other embodiments, at least one (or all) of $R^1$, $R^3$, and $R^4$ is a linear, branched, or cyclic alkyl group containing precisely or at least 3, 4, 5, 6, 7, 8, 9, 10, 11, or 12 and up to 14, 16, 18, 20, 22, 24, 26, 28, or 30 carbon atoms, or an alkyl group containing a number of carbon atoms within a range bounded by any two of the foregoing values (e.g., 3-30, 4-30, 6-30, 8-30, 10-30, 12-30, 3-20, 4-20, 6-20, 8-20, 10-20, or 12-20 carbon atoms).

Examples have been set forth below for the purpose of illustration and to describe certain specific embodiments of the invention. However, the scope of this invention is not to be in any way limited by the examples set forth herein.

EXAMPLE 1

Process Exemplifying Scheme 2

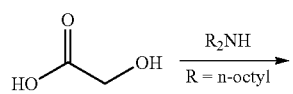

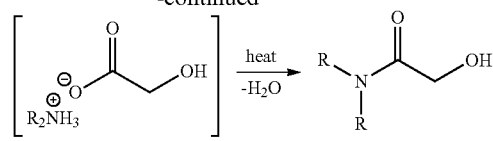

In a round bottom flask equipped with a magnetic stir bar, 1.0 eq of glycolic acid and 1.0 eq of dioctylamine were mixed in o-xylene. The reaction mixture was heated slightly (>50° C.) to dissolve the dioctylamine in o-xylene. Upon dissolution of dioctylamine, immediate formation of precipitate (salt) was observed. To the round bottom flask was attached a Dean-Stark apparatus with a condenser. The formed salt was then heated to 150° C. or greater to remove in-situ formed water. After heating overnight, the o-xylene was distilled off. Hexanes where then added to the residue, the solution was filtered to remove traces of salt (i.e., salt is not soluble in hexanes), and the solvent (hexanes) was removed under reduced pressure. The obtained orange oil (glycolamide) was used in the next step without any further purification. Reaction yield was >91%.

EXAMPLE 2

Another Process Exemplifying Scheme 2

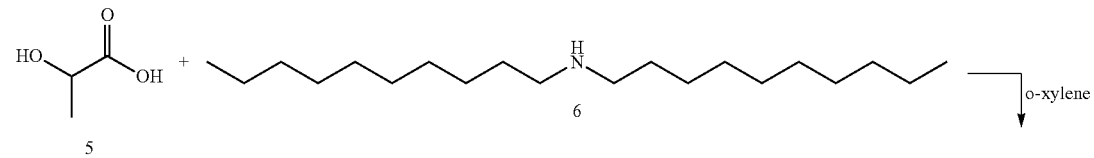

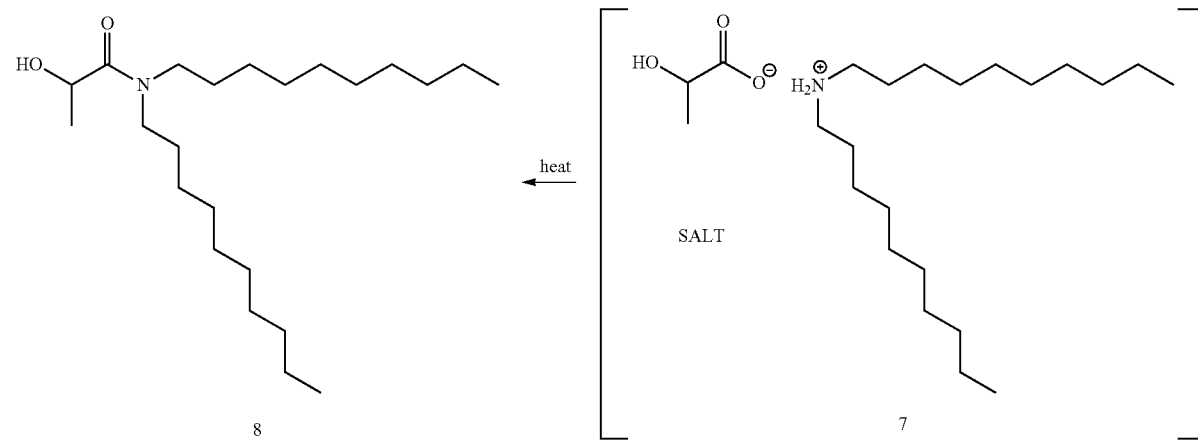

Secondary amine (6, 444.0 g, 1.0 equiv.) was dissolved in 300 mL of o-xylene in a round bottom flask equipped with Dean-Stark apparatus and condenser. The mixture was heated (up to 50° C.) to facilitate the dissolution of 6. Then, 5 (134.4 g, 1.0 equiv.) was added in portions (the salt formation is slightly exothermic). Afterwards, the reaction mixture was heated at 150° C. for 12 hours. An aliquot was taken and analyzed using $^1$H NMR spectroscopy, which showed that ⅓ of the salt 7 remains. The reaction mixture was then heated at 210° C. for another 12 hours. The consumption of 7 was confirmed using $^1$H NMR spectroscopy. The solvent was then removed via simple distillation and the residue was heated at 70° C. under high vacuum to remove trace amounts of solvent. The product 8 was obtained as a light orange oil (540 g, 98% yield).

EXAMPLE 3

Process Exemplifying Scheme 5 for Producing Cyclic DGA Compounds

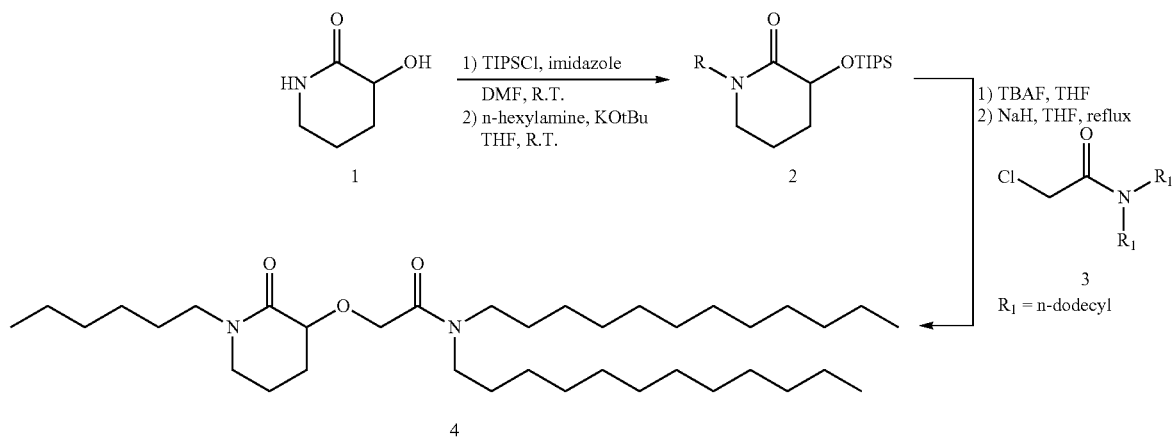

1-hexyl-3-((triisopropylsilyl)oxy)piperidin-2-one: 2

3-hydroxypiperidin-2-one 1 (2.5 g, 0.02 mol) and imidazole (1.05 equiv) were dissolved in anhydrous DMF (0.2 M). To this solution was then added TIPS-Cl (1.05 equiv) and the reaction mixture was stirred at room temperature for 12 hours. To the reaction mixture was added water and product was extracted with E$_2$O (3×). The combined organic phase was washed with brine, dried over MgSO$_4$, filtered, and the solvent was removed under reduced pressure. The product was used in the next step without further purification. To the ice-cold solution of the TIPS protected product (5.9 g, 0.02 mol) in anhydrous THF (0.2 M) was added tBuOK (2.68 g, 0.02 mol). The reaction mixture was stirred for 30 min before the addition of n-hexyl iodide. Afterwards, the reaction mixture was stirred for 12 hours at room temperature. To the reaction mixture was added water and product was extracted with E$_2$O (3×). The combined organic phase was washed with brine, dried over MgSO$_4$, filtered, and solvent removed under reduced pressure. The product (2) was used in the next step without further purification.

N,N-didodecyl-2-((1-hexyl-2-oxopiperidin-3-yl)oxy)acetamide: 4

To 1-hexyl-3-((triisopropylsilyl)oxy)piperidin-2-one 2 (0.02 mol) dissolved in anhydrous THF (0.4 M) was added TBAF (1 M in THF, 1.2 equiv). The reaction mixture was stirred at room temperature for 12 hours. Afterwards, the solvent was removed under reduced pressure and product was purified on CombiFlash® R$_f$ automated flash chromatography system using normal phase silica gel as a stationary phase and gradient 0-80% EtOAc in hexanes as an eluent system to yield light yellow oil (3.9 g, 90%). Next, the round bottom flask was charged with NaH (0.25 g, 6.3 mmol) and anhydrous THF (0.2 M) under inert atmosphere. To the reaction mixture was then added dropwise the above obtained product (1.26 g, 6.3 mmol) dissolved in 5 mL of anhydrous THF. The reaction mixture was stirred at room temperature for 30 minutes. Afterwards, 2-chloro-N,N-didodecylacetamide 3 (3.0 g, 6.3 mmol) dissolved in anhydrous THF (5 mL) was added to the reaction mixture. The reaction mixture was heated at 35° C. for 12 hours. To the reaction mixture was added water and product was extracted with E$_2$O (3×). The combined organic phase was washed with brine, dried over MgSO$_4$, filtered, and solvent removed under reduced pressure. and product was purified on CombiFlash® R$_f$ automated flash chromatography system using normal phase silica gel as a stationary phase and gradient 0-80% EtOAc in hexanes as an eluent system to yield light yellow oil (2.7 g, 73%). $^1$H NMR (400 MHz, CDCl$_3$) 4.73-4.55 (m, 2H), 4.00-3.92 (m, 1H), 3.38-3.05 (m, 8H), 2.24-2.12 (m, 1H), 2.07-1.94 (m, 2H), 1.86-1.65 (m, 3H), 1.60-1.45 (m, 6H), 1.35-1.18 (m, 40H), 0.93-0.83 (m, 9H). $^{13}$C NMR (100.67 MHz, CDCl$_3$) δ 170.2, 169.8, 75.4, 69.3, 47.8, 47.5, 47.1, 46.3, 32.1, 31.7, 29.8, 29.7, 29.7, 29.6, 29.5, 28.9, 28.4, 27.7, 27.2, 27.03, 27.01, 26.7, 22.8, 22.7, 19.8, 14.3, 14.2.

While there have been shown and described what are at present considered the preferred embodiments of the invention, those skilled in the art may make various changes and modifications which remain within the scope of the invention defined by the appended claims.

What is claimed is:

1. A method for producing a diglycolamide molecule having the formula:

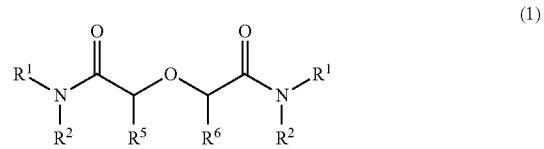

(1)

wherein $R^1$ and $R^2$ are independently selected from alkyl groups (R) and acyl groups (C(O)R) in which the alkyl groups (R) contain 1-30 carbon atoms and optionally contain an ether or thioether linkage between carbon atoms, and $R^5$ and $R^6$ are independently selected from hydrogen atom and alkyl groups containing 1-3 carbon atoms; and one or both pairs of $R^1$ and $R^2$ are optionally interconnected to form a ring;

the method comprising: combining a diglycolic acid molecule (A) and a secondary amine (B) to form a salt intermediate (C), and heating the salt intermediate (C) to a temperature of 100° C. to 300° C. to form the diglycolamide of Formula (1) in a dehydration process, wherein the method is shown schematically as follows:

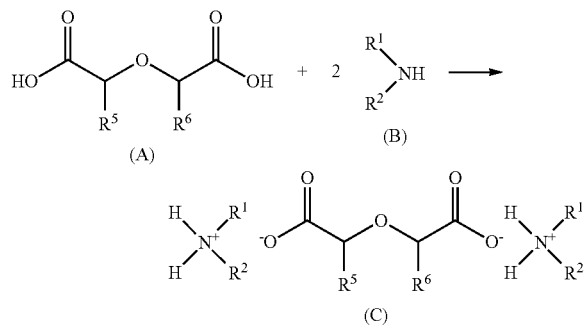

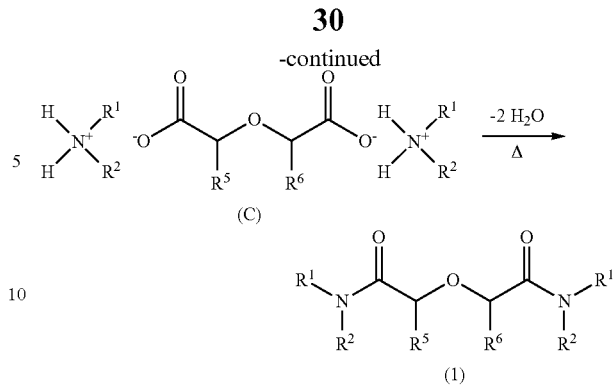

2. The method of claim 1, wherein $R^5$ and $R^6$ are hydrogen atoms.

3. The method of claim 1, wherein $R^5$ and $R^6$ are methyl groups.

4. The method of claim 1, wherein $R^1$ and $R^2$ are the same.

5. The method of claim 1, wherein $R^1$ and $R^2$ are different.

6. The method of claim 5, wherein $R^1$ contains 1-3 carbon atoms and $R^2$ contains 4-30 carbon atoms.

7. The method of claim 1, wherein (A) and (B) are combined with a solvent having a boiling point of at least 100° C.

8. The method of claim 1, wherein (A) and (B) are ball milled in the absence of a solvent.

* * * * *